US012806382B2

(12) United States Patent
Roche Rebollo et al.

(10) Patent No.: US 12,806,382 B2
(45) Date of Patent: Nov. 24, 2026

(54) MEDICAL INSTRUMENT SUPPORT DEVICE

(71) Applicant: VASCULAR BARCELONA DEVICES, S.L., Barcelona (ES)

(72) Inventors: Enrique Roche Rebollo, Barcelona (ES); Guiu Llusa Melendez, Barcelona (ES)

(73) Assignee: VASCULAR BARCELONA DEVICES, S.L., Barcelona (ES)

( * ) Notice: Subject to any disclaimer, the term of this patent is extended or adjusted under 35 U.S.C. 154(b) by 789 days.

(21) Appl. No.: 17/748,586

(22) Filed: May 19, 2022

(65) Prior Publication Data

US 2022/0273914 A1 Sep. 1, 2022

Related U.S. Application Data

(63) Continuation of application No. PCT/EP2020/050645, filed on Nov. 2, 2020.

(30) Foreign Application Priority Data

Nov. 20, 2019 (EP) .................................... 19383022

(51) Int. Cl.
*A61M 25/09* (2006.01)
*A61M 5/14* (2006.01)

(52) U.S. Cl.
CPC .... *A61M 25/09041* (2013.01); *A61M 5/1418* (2013.01); *A61M 2209/084* (2013.01)

(58) Field of Classification Search
CPC .......... A61M 25/09041; A61M 5/1418; A61M 2209/084; A61M 2025/028;
(Continued)

(56) References Cited

U.S. PATENT DOCUMENTS 4,250,880 A * 2/1981 Gordon ................. A61M 25/02 128/DIG. 26
4,606,735 A 8/1986 Wilder et al.
(Continued)

FOREIGN PATENT DOCUMENTS

CN 202459758 U 10/2012
DE 20213004 U1 11/2002
(Continued)

OTHER PUBLICATIONS

Chinese Office Action with English translation, Application No. 202080078325.5, Jun. 29, 2024, 30 pages.
(Continued)

*Primary Examiner* — Theodore J Stigell
*Assistant Examiner* — Benjamin Koo
(74) *Attorney, Agent, or Firm* — Edell, Shapiro & Finnan, LLC

(57) ABSTRACT

A device for supporting an elongated medical instrument that includes a base, a gripping system for securing the base to a surgical towel, and at least two retaining members disposed on the base and extending upwardly from the base. Each of the retaining members has a slit configured to support the medical instrument, such that the medical instrument extends through the slit of the retaining members substantially along a first direction, and wherein a first of the at least two retaining members is disposed behind a second of the retaining members substantially along the first direction.

12 Claims, 13 Drawing Sheets

(58) Field of Classification Search
CPC .. A61M 2025/024; A61M 2025/09125; A61M 25/02; Y10T 24/23; A61B 2046/234
See application file for complete search history.

(56) References Cited

U.S. PATENT DOCUMENTS

| | | | | |
|---|---|---|---|---|
| 4,997,421 | A | 3/1991 | Palsrok et al. | |
| 5,239,193 | A | 8/1993 | Skakoon | |
| 5,833,667 | A | 11/1998 | Bierman | |
| D453,294 | S * | 2/2002 | Bitzer | D8/395 |
| 7,229,051 | B2 | 6/2007 | Mailhot, Jr. | |
| 8,366,638 | B2 | 2/2013 | Teirstein | |
| 8,523,824 | B2 | 9/2013 | Teirstein et al. | |
| 8,679,065 | B2 | 3/2014 | Schuman et al. | |
| 8,827,959 | B2 | 9/2014 | Wright et al. | |
| 9,895,486 | B1 | 2/2018 | Carey-Hench | |
| 2002/0177869 | A1 | 11/2002 | Eidenschink et al. | |
| 2005/0182368 | A1 | 8/2005 | Gillis et al. | |
| 2006/0180714 | A1 | 8/2006 | Mailhot, Jr. | |
| 2006/0217669 | A1 | 9/2006 | Botha | |
| 2010/0010475 | A1* | 1/2010 | Teirstein | A61M 25/02 604/528 |
| 2010/0274158 | A1* | 10/2010 | Teirstein | A61M 25/09 264/294 |
| 2012/0029484 | A1* | 2/2012 | Gusmao | A61M 25/02 604/538 |
| 2018/0156361 | A1 | 6/2018 | Honeycutt | |
| 2019/0307990 | A1 | 10/2019 | Fogg et al. | |

FOREIGN PATENT DOCUMENTS

| | | |
|---|---|---|
| JP | 2011527609 A | 11/2011 |
| WO | 2010006037 A1 | 1/2010 |

OTHER PUBLICATIONS

International Search Report, PCT/EP2020/080645, Feb. 2, 2021, 4 pages.
Japanese Office Action with English Translation, Application No. 2022-528255, Sep. 10, 2024, 5 pages.
Canadian Office Action, Application No. 3,158,681, Jan. 23, 2024, 8 pages.
Chinese Office Action with English translation, Application No. 202080078325.5, Dec. 19, 2023, 28 pages.

* cited by examiner

MEDICAL INSTRUMENT SUPPORT DEVICE

CROSS-REFERENCE TO RELATED APPLICATIONS

The present application relates to and claims the benefit and priority to International Appl. No. PCT/EP2020/080645, filed Nov. 2, 2020, which claims the benefit and priority to European Appl. No. EP19383022.1, filed Nov. 20, 2019.

TECHNICAL FIELD

The present disclosure generally relates to devices for supporting medical instruments, and, more specifically, to support devices for supporting elongate medical instruments, such as guidewires and catheters and others.

BACKGROUND

Nowadays, the tendency of the medical world is focused on the introduction of new technologies for a better healthcare delivery to patients. Open surgeries are being used less frequently and minimally invasive procedures are now being favored by patients and doctors. Minimally invasive procedures offer the potential benefit of less risk of infection, shorter recovery time, less scarring and less pain for the patient.

Minimally invasive procedures, such as endovascular repair, angioplasty etc., may involve various different instruments, such as guidewires, catheters, balloons and stents. Such procedures may use a known technique (Seldinger technique) to access a vein or organ. In this technique a needle is used to make a small puncture in the skin in order to gain access to an artery, and a guidewire passes through the incision in order to reach any part of the human anatomy that needs investigation or treatment (angioplasty, recanalization, stent implantation, etc.). The guidewire may first reach a treatment site. Then, a treatment catheter, a balloon catheter or a stent can be delivered to the treatment site by passing over the guidewire. Using imaging such as ultrasound or fluoroscopy (X-ray video), a specialist guides the medical instruments to said treatment site. In order to enable the catheters to be inserted and reach the treatment site, expanders, or introducers may be used to ensure that the incision in the skin is large enough. The use of guiding catheters to guide further instruments is also known.

Thus, the guidewires provide a passage to the treatment site of a hollow organ that the specialists use in order to introduce other medical instruments. Once the guidewire and/or other medical instrument is in place, they generally need to stay in place. Otherwise an operation may not be carried out properly.

Maintaining the guidewire and/or other instruments in the desired position on the treatment site, or maintaining the guidewire in place, is a vital issue while performing such interventions. However, there is always a risk of unintentionally moving a catheter, or a guidewire. If the correct position of the medical instruments is lost, in order to continue with the surgical procedure, the specialist has to relocate the guidewire and/or the other medical instruments in the operating field (treatment site). This prolongs the procedure and may increase the risk for the patient and the specialist, e.g. prolonged anesthetics or by a higher exposition to X-rays radiation due to the use of fluoroscopy, amongst others.

Currently, specialists implement the typical method of using layers of wet sterile towels to secure the medical instruments in a fixed position when performing an intervention. The bulky layers of towels are difficult to control, and, thus, the instruments are prone to moving, thus resulting in an unreliable method.

In the prior art, devices have been proposed for holding guidewires, catheters and/or the like, in a fixed position during an intervention. In particular, document U.S. Pat. No. 8,523,824 refers to devices, systems and methods for catheter and guidewire management in a surgical setting. Such devices include retaining member housings and retaining members that are mounted into the housing, wherein such retaining members can retain one or more guidewires, catheters or the like. These devices are rather complicated and they may be considered for an endovascular procedure in which numerous medical instruments will be needed.

Document U.S. Pat. No. 8,366,638 refers to a device for loading a guidewire into a tubular instrument such as a catheter.

Therefore, there is still a need for a device that can retain medical instruments and resolve at least some of the aforementioned problems.

SUMMARY

In a first aspect, a device configured to support elongated medical instruments is provided. The device comprises a base, a gripping system for securing the base to a surgical towel and at least two retaining members disposed on the base and extending upwardly from the base. The retaining members have a slit configured to retain the elongated medical instrument, such that the elongated medical instrument extends through the slit of the retaining members substantially along a first direction. A first of the at least two retaining members is disposed behind a second retaining member substantially along the first direction.

The support device may be fixed in position by gripping a surgical towel. Preferably the elongated medical instrument is fixed in position in the direction of the elongated instrument with the retaining members providing retaining support at two locations, one behind the other, of the elongated instrument. Alternatively, one of the retaining members is used for retaining one instrument, e.g. a catheter, and the other is used for another elongated medical instrument e.g. a guidewire around which the catheter is arranged. The two retaining members allow for moving or removing one of the medical instruments, while leaving the other one firmly in place.

Surgical towel as used herein may be understood to comprise any type of cloth or fabric, including e.g. cotton that is used in surgeries, e.g. to delimit a treatment area. Surgical towels may be absorbent or impermeable and may be disposable or re-usable.

In an example, the retaining members of the device may comprise slits of different shapes. The slits of the retaining members may comprise a first, a second and a third segment, wherein the first segment may have a constant width. The width of the first segment may depend on the range of the diameters of the elongated medical instruments. The second segment may have a substantially V-shaped cross section. Said second segment may be formed of two surfaces, wherein such surfaces form an angle, and wherein said angle may depend on the range of the diameters of the elongated medical instruments. And the third segment may have a rounded or ovaloid cross section, wherein the dimensions of the cross section may depend on the diameters of the medical instruments to be used. The different shapes of the slits can increase versatility and allow the device to be used many different types of interventions by retaining elongated medical instruments of different dimensions.

The support device may comprise at least two retaining members having slits with the same shapes, while, in other examples, the device may comprise retaining members wherein one of the at least two retaining members has a different shape and/or dimensions than the other such that to receive different elongated medical instruments in each slit. In further examples, the support device may comprise retaining members with more than one slit, providing support for more than one elongated instrument. Such support devices with retaining members with slits of different shapes and sizes provide a device that be used to fix in position a plurality of elongated medical instruments of different diameters. The different shapes of the slits provide a versatile medical instrument support device for supporting elongated medical instruments, thus, increasing its usability.

In some examples, the retaining members may be detachably fixed to the base of the support device. Such a support device permits the exchange of the retaining members and facilitates the immobilization of the several different instruments (of different type, shape or size) that may be required in the progress of a surgical intervention. Maintaining the base gripped on a surgical towel and only changing the retaining members of the device facilitates surgical interventions and contributes to a desirable reduction in surgery time.

In other examples, the at least two retaining members may be of single-use (i.e. disposable) facilitating a less time-consuming intervention, therefore, it will be easier for an operator to detach and attach new, sterilized retaining members rather than having to sterilize already used retaining members.

In a further example, a support device is provided, wherein the gripping system for securing it in place may be formed by an incision made on the base such that at least one channel is formed on the base substantially along the first axis, wherein said channel may have a sinusoidal shape such as to secure the device onto the fabric. The channel may comprise an opening, wherein said opening may be located in a side of the device perpendicular to the first axis, and wherein the channel may be formed alongside the retaining members. Such a shape of the channel allows the device to be secured to a surgical towel or any other piece of cloth in an efficient manner, and, also permits the operator to move the device along the towel as may be required to maintain the position of the elongated medical instruments in the operating field. Thereby a device with improved handling is provided, enabling operators to perform more precise and efficient interventions.

In other examples, a support device is provided, wherein the gripping system may comprise two channels, wherein said channels may optionally extend substantially along the first axis such that the retaining members are located in-between said channels, and, wherein the orientations of said two channels may be arranged in an opposite way such that the openings of the two channels are located on different sides of the base, wherein said sides extend generally perpendicular to the first axis. This provides a support device with an improved ergonomic design, thus, enhancing its function and increasing its usability.

In some other examples, the base adjacent to the opening of the channel may comprise at least one portion with increased roughness. The shape and the surface texture of such a portion can improve the manipulation of the device by the operator, especially when such device is wet during an intervention.

In some examples, the elongated medical instruments may be guidewires and/or catheters.

These and other features and advantages of the present disclosure will become apparent from the following description of particular examples, when viewed in accordance with the accompanying drawings and appended claims.

DETAILED DESCRIPTION

Figure 1A:
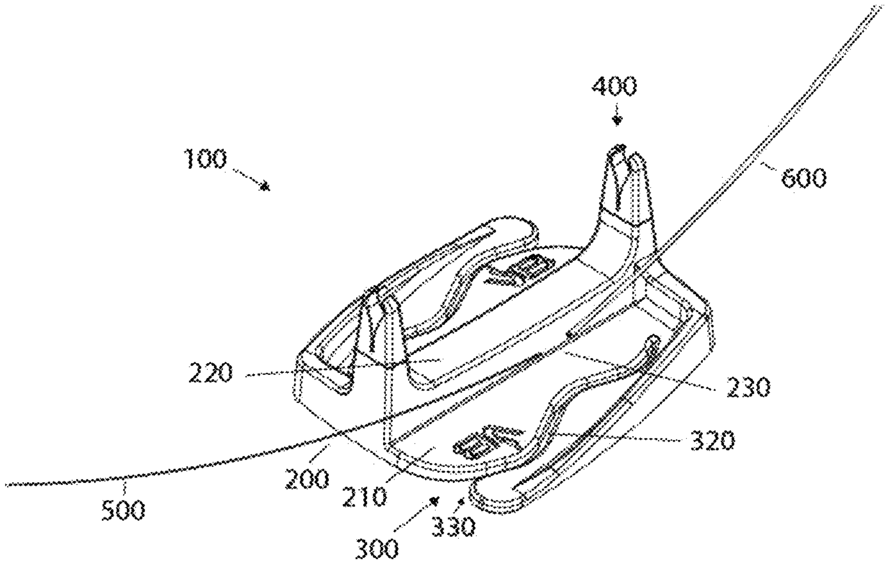
FIG. 1A illustrates an isometric view of a device for supporting an elongated medical instrument and medical instruments on the support device in accordance with an example of the present disposure.
Figure 1B:
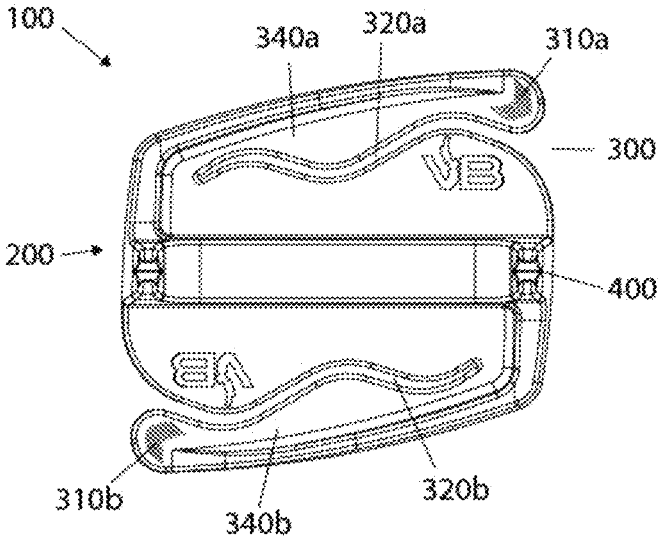
FIG. 1B illustrates a top view of the support device according to one embodiment.

FIGS. 1A and 1B schematically illustrate an isometric and a top view of an example of a support device 100 for supporting an elongated medical instrument. The support device 100 comprises a base 200, a gripping system 300 and two retaining members 400. The base 200 in this example comprises a flat portion 210 and an elevated portion 220, which is located in the middle of the flat portion 210.

In this particular example, retaining members 400 may be integrally formed with base 200. As will be explained in more detail hereinafter, the retaining members serve to retain a medical instrument, such as e.g. a guidewire or catheter. The support device may be fixed in place on an operating table. The gripping system 300 may be used for that purpose as will be explained hereinafter as well. If the device is fixed on an operating table, the medical instrument retained in it (e.g. guidewire, catheter) may also be fixed in place. Unplanned and undesired movements of the medical instruments may be avoided.

The base, and in particular the flat portion 210 of the base 200, as shown in FIG. 1A, may comprise one or more open grooves 230 for guidewire threading and a gripping system 300. The groove 230 for guidewire threading is configured to receive medical instruments, e.g. a guidewire 500 and a catheter 600, to facilitate an end of the guidewire passing through an open end of the catheter, that is, the groove 230 may be sized and shaped such that a medical professional can thread the guidewire into the open end of the catheter. The groove 230 may be formed integrally with the base 200 of the device 100. In this example, a groove 230 is depicted to be formed close to the central elevated portion 220 of the base 200 and between the gripping system and the retaining members, in particular, at the inflection point of the transition of the base from the flat to the elevated portion. The sidewall of the central elevated portion may thus be used as a support in a guidewire threading procedure.

The groove 230 may have a substantially semi-circular cross-section with different radii and depths depending on the dimensions of the medical instruments. The radius of the groove 230 may substantially match the exterior radius of the medical instrument with the greatest radius (catheter), which is received by the groove, and the depth of the groove may be greater than the exterior diameter of the catheter.

The gripping system 300 may be formed integrally with the base 200 of the device. In some examples, an opening 330 is provided on an edge of the base 200 that extends inwards into the base. A channel 320 may thus be formed extending substantially along a length of the device. FIG. 1B illustrates a device wherein the base 200 comprises two channels 320*a*, 320*b* of a sinusoidal shape, each starting at an opposite edge and extending in opposite directions. The sinusoidal shape facilitates gripping a surgical towel, which can be inserted from the opening at the edge and forced into the channel to be firmly stuck in the channel. The support device may thus be fixed with respect to a surgical towel draped onto and/or next to a patient. The position of the support device may thus be fixed. A medical instrument that is fixed in the retaining members will thus also be fixed in a given position. Moreover, when an operator of the device desires to change its position, such a sinusoidal shape enables a relatively smooth sliding of the device 100 with respect to the surgical towel 700.

The gripping system in this example includes two channels which allow insertion of a surgical towel from opposite directions. The gripping system may also comprise portions 310*a*, 310*b* that may have a surface with increased roughness to facilitate gripping by a user, e.g. a nurse or doctor.

In one example, the support device may be configured to be re-used. After an intervention, the device may be sterilized and prepared for a next intervention. In other examples, device is disposable and configured for single use only.

Support devices may be made from one or more thermoplastic materials. Suitable thermoplastic materials include Acrylic, ABS, Nylon, PLA, Polybenzimidazole, Polycarbonate, Polyether sulfone, Polyoxymethylene, Polyetherether ketone, Polyetherimide, Polyethylene, Polyphenylene oxide, Polyphenylene sulfide, Polypropylene, Polystyrene, Polyvinyl chloride, Polyvinylidene fluoride, Teflon, any of their derivatives and combinations thereof. Support devices may also be made of thermosetting polymers. Suitable thermosetting polymers include Polyester, Polyurethanes, Polyureaings, Vulcanized rubber, Bakelite, Duroplast, Urea-formaldehyde, Melamine, Diallyl-phthalate, Epoxy resin, Epoxy novolac resins, Benzoxazines, Polyimides, Bismaleimides, Cyanate esters, polycyanurates, Furan resins, Silicone resins, Thiolyte, Vinyl, derivatives and combinations thereof. The support devices may also be made from metals commonly used in the manufacture of medical devices. Suitable metals include stainless steel, and titanium.

Both fingers 340*a* and 340*b* may comprise portions 310*a* and 310*b* with higher roughness than the rest of the base 200. This provides a support device 100 that can be gripped easily by an operator, and, moreover, can be held and manipulated with greater accuracy, especially if the portions 310*a*, 310*b* are wet during an intervention, or have saline or body fluids on them. Said rough portions 310*a* and 310*b* may be part of the fingers 340*a* and 340*b*, respectively, and are located near the openings 330*a* and 330*b* of the channels. The shape and the surface texture of said portion may be formed such that the device to be held easily by an operator, thus, providing a more efficient manipulating of the device.

Figure 3A:
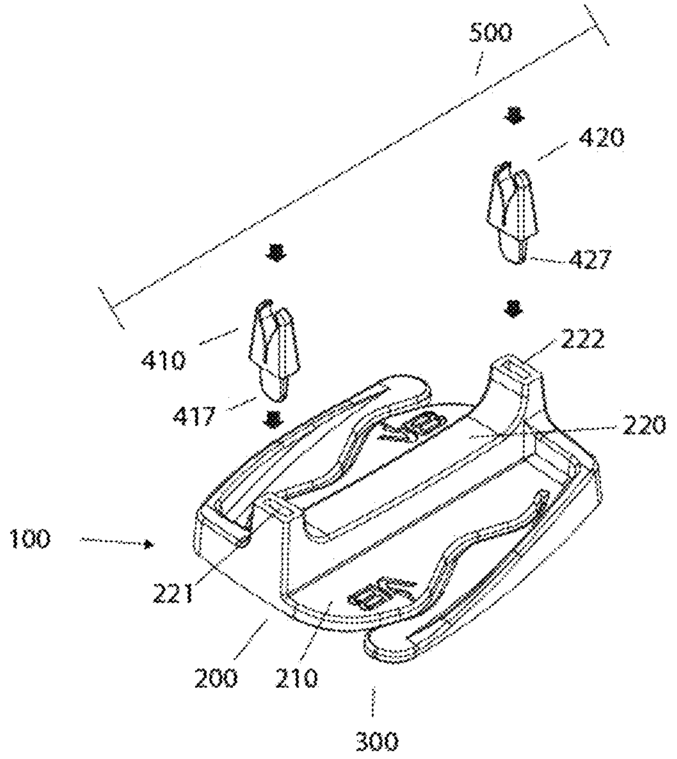
FIG. 3A illustrates another example of a support device for supporting an elongated medical instrument having two detachably fixed retaining members.
Figure 3B:
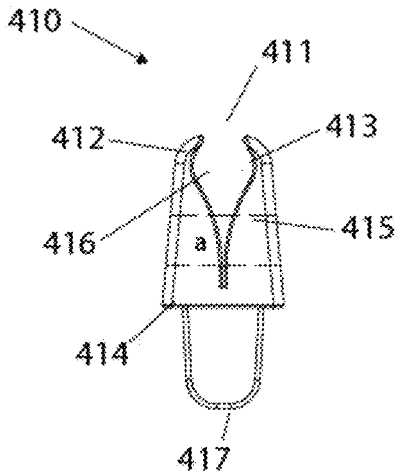
FIG. 3B illustrates a detachably fixed retaining member of the example shown in FIG. 3A.
Figure 3C:
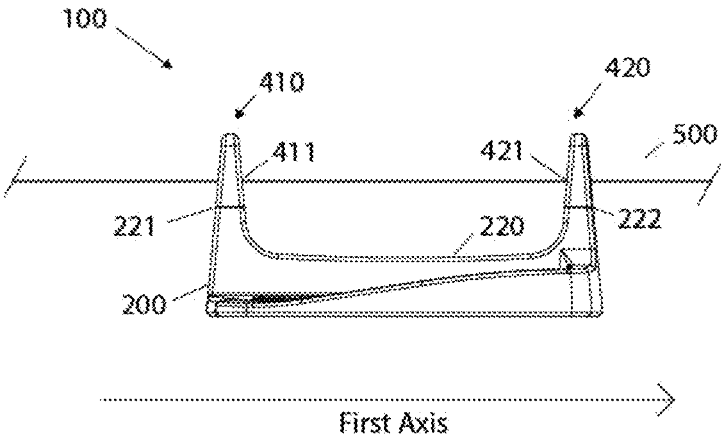
FIG. 3C illustrates a side view of the support device of FIG. 3B.

Support device 100 comprises at least two retaining members 410, 420, as shown in FIGS. 3A and 3C. Particularly, FIG. 3A illustrates an example in which the retaining members are detachably fixed to the base 200. The detachable retaining members 410, 420 may be placed in couplings 221 and 222 by a user, wherein said couplings may be part of the elevated portion 220 of the base 200. The retaining members comprise corresponding connections 417, 427 that connect the retaining members 410, 420 with the base 200 by fixing them to said couplings. In this particular example, the coupling between retaining members 410, 420 and the couplings 417, 427 is a male-female coupling. In this particular case, the retaining members 410, 420 have male coupling portions, and the base comprises female coupling portions for receiving the retaining members. Other couplings, coupling portions, and connectors are of course possible.

FIG. 3B illustrates the retaining member 410 in more detail. The retaining member 410 of this example comprises surfaces 412, 413, which form an opening, slit 411. The slit 411 is formed at the upper end of the retaining member 410 in order to receive medical instruments, such as catheters, guidewires etc. In this example, the slit 411 is shown to comprise three different segments 414, 415, 416, wherein each segment is shaped and sized differently.

Slit 411 is depicted to be made up of a first segment 414, which has a small opening with a constant width. Particularly, surfaces 412, 413 of slit 411 are formed parallel to each other along the first segment 414, thus, forming an opening with a cross-section of a constant width, suitable for holding medical instruments that may be used during an intervention. Such a segment 414 may be closer to the connection point 417, i.e. at a bottom or lower segment of slit 411. The first segment of the slit may particularly be used for retaining elongated instruments with the smallest cross-section.

Above the first segment, a second segment 415 of the slit 411 is shown, wherein the surfaces 412, 413 form a substantially V-shaped cross section. The surfaces may form an angle $\alpha$ appropriate for receiving medical instruments of different diameters. Thus, a suitable angle may be selected depending on the types of instruments to be retained. By pushing instruments downwards into the slit, the medical instruments may become retained. A suitable angle may be between 2° and 20°, and specifically between 3° and 15°. The V-shape with varying width of the cross-section enables elongated medical instruments of different cross-sections to be retained. If a medical instrument is relatively small, it will not become retained along the second segment 415 but rather at the thinnest segment 414.

In this example, another segment, a third segment 416, is formed above the other two segments 415 and 414. The third segment comprises a rounded, ovalloid or somewhat O-shaped cross section formed by a variety of curvatures that can be provided by the surfaces 412, 413. The rounded or ovaloid cross-section may be configured to retain a standard end of a catheter. A variety of different shapes in one slit 411 such as shown in this example provides a device with different retaining effects to the medical instruments, and, makes it possible for a plurality of different medical instruments of different sizes to fit into the slits of the retaining members.

Slits may be configured to support medical instruments, such as guidewires, catheters, etc. Each medical instrument has different dimensions depending on the expected uses, e.g., type of intervention, therefore, having different segments within the slits with different cross-sections permit for the retention of medical instruments necessary in any type of intervention. For example, the guidewires that are typically used may have different diameters, e.g. 0.038", 0.035", 0.018", 0.014". The guidewires may have a diameter in the range from 0.254 mm (0.010") to 0.965 mm (0.038"), while the catheters may have diameters ranging from e.g. 3 French gauge (1 mm) to 34 French gauge (11.33 mm) depending on the expected uses. Alternative shapes and dimensions of the slits will be shown later.

The dimensions of the slits (thickness and/or angle and/or diameter) may be chosen in relation with the medical instruments to be retained. Other aspects may also contribute to the retaining efficiency of such device. The retaining members may be made of materials that also contribute to the efficiency of the device, as for example, the use of flexible rubber-like materials so as to retain the medical instruments without a need to adapt precisely to the diameters of such instruments.

In any of the embodiments disclosed herein, slits or portions of the slits may receive a specific treatment to increase roughness. For example, the mold for injection may undergo a local chemical etching treatment to provide the mold with texture locally.

In any of the embodiments disclosed herein, near a bottom of the slit, one or more small grooves may be provided in the mold used for injection. Such small grooves may result in small notches in the sidewalls of the slit of the support device. These notches can help retain the smallest guidewires. The grooves in the molds may be manufactured using EDM (electrical discharge machining).

A support device 100, comprising two detachably fixed retaining members 410, 420, is illustrated in FIGS. 3A and 3C. As mentioned before, the retaining members 410, 420 are attached onto the base 200 by fixing the connections or connectors 417, 427 into the couplings or coupling recesses 221 and 222, and the slits 411, 421 of the retaining members are configured to support the medical instruments. As FIG. 3C depicts, a medical instrument, e.g. a guidewire 500, is fixed in the slits of the retaining members 410, 420 at two points along its length and is extended through the slits 411, 421 substantially along a first axis, wherein the retaining members are disposed substantially behind one another along such first axis. It will be clear that in this example the first axis extends along the longitudinal length of the base. The configuration of support device 100, comprising at least two retaining members that hold a medical instrument (in this case guidewire 500) at two points, provides a firmer retention of the medical instrument. A firm support of the medical instrument allows the operator to safely and effectively carry out other tasks without displacement of the medical instrument. Therefore, support device 100 provides a safe and effective way to carry out surgical interventions involving medical instruments that benefit greatly from immobilization in the surgical field.

The flexibility of the retaining members in combination with the different cross-sections of the segments of the slits permits a medical instrument support device to engage elongated medical instruments of different dimensions. In this aspect, the retaining members may comprise slits with one, two or three segments, wherein each segment may have a cross-section of a different shape. FIGS. 4A to 4D illustrate retaining members with slits of alternative shapes.

Figure 4A:
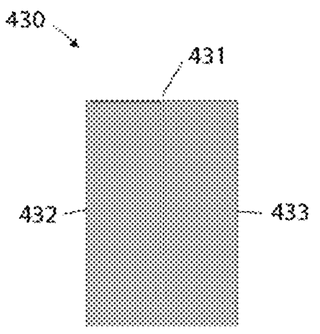
FIGS. 4A, 4B, 4C and 4D illustrate detachably fixed retaining members of different shapes which may be used in examples of the present disclosure.

FIG. 4A illustrates a retaining member 430 comprising a slit 431 having a constant cross-section. The slit 431 is formed by two surfaces 432, 433 that are parallel to each other, thus, forming a cross-section with a constant width. The width of such slit may be chosen in relation with the different diameters of the medical instruments used during an intervention. The material(s) of the retaining member may contribute supporting medical instruments of different diameters, as for example, an elastic, resilient, or flexible rubber-like material may provide a retaining member that can be implemented for instruments of a wide range of diameters. Similar material(s) may be used for the retaining members depicted in FIG. 4*b*-4*d*.

Figure 4B:
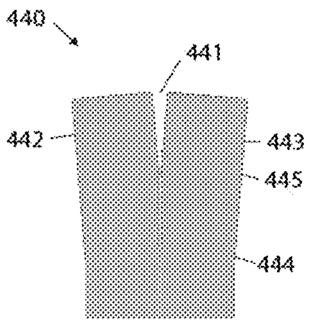

Retaining member 440 with slit 441 illustrated in FIG. 4B. In this example, the slit comprises two segments 444, 445 with cross sections of two different shapes. The first segment 444 has a small cross-section with a constant width, as shown in FIG. 4A. While above the first segment, a second segment 445 is formed by two surfaces 442, 443 forming an angle, suitable for receiving medical instruments of different diameters, as also has been described in FIG. 3B.

Figure 4C:
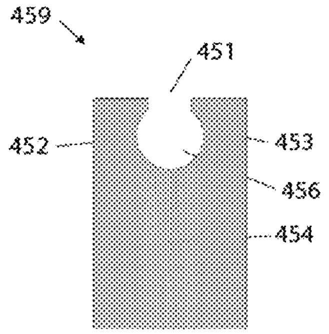

FIG. 4C shows another example of a retaining member 450, wherein the slit 451 of such a retaining member comprises two segments as well. The first segment 454 has a small cross-section with a constant width, as shown in FIG. 4A, while above the first segment, another segment 456 is formed. Such segment comprises a substantially O-shaped cross section formed by the surfaces 452, 453, as also has been described in FIG. 3B. The O-shaped segment may have a diameter that is selected on the basis of the diameters of the medical instruments. Other aspects of such slits (materials, sizes, dimensions) could be the same as in the various examples described hereinbefore.

Figure 4D:
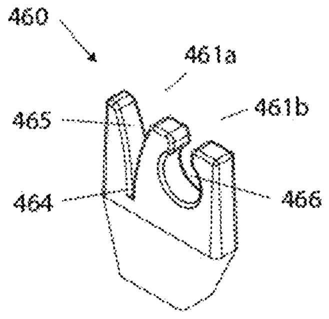

Yet another example of a retaining member 460 is presented in FIG. 4D. The retaining member 460 of this example has two slits 461*a*, 461*b* arranged next to each other. In this case, the two slits together comprise three different segments, as illustrated in FIG. 3B, but with a different configuration. That is, slit 461*a* comprises segments 464 and 465 with a configuration illustrated in FIG. 4B, and slit 461*b* comprises an O-shaped segment 466. Retaining member 460 has bigger dimensions than the other retaining members beforementioned. This configuration allows the engagement of more than one elongated instrument in the device simultaneously.

The before mentioned figures depict retaining members comprising a variety of slits comprising different segments with cross-sections of different shapes, thus, providing a device that can be implemented with a plurality of medical instruments of different diameters. Although the devices described hereinbefore comprise at least two retaining members having slits with the same shapes, other alternative devices are possible.

Figure 5:
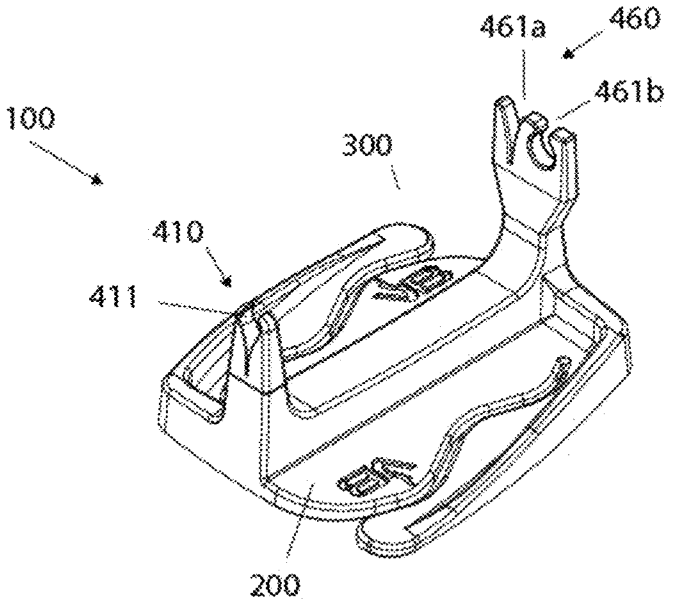
FIG. 5 illustrates an isometric view of a further example of a support device for supporting an elongated medical instrument.

FIG. 5 illustrates a support device 100 with a base 200 and a gripping system 300 integrally formed with the base 200.

Device 100 also comprises two detachably fixed retaining members 410, 460, wherein the retaining member 410 comprises a slit 411 that is different from the slits 461*a*, 461*b* of the retaining member 460. In particular, retaining member 410 has a slit 411 as described in FIG. 3B, while the shape of the slits 461*a*, 461*b* of the retaining member 460 are formed as the retaining member illustrated in FIG. 4D. The use of such retaining members renders device 100 a versatile device for supporting elongated medical instruments of different dimensions, thus increasing the usability of device 100. In this example, retaining members 410, 460, and, especially retaining member 460 may support more than one elongated medical instrument due to the multiple positions available for receiving such instruments. Alternative combinations of different slits on the retaining members may also be used for device 100. Such retaining members may be made of material(s) that contribute to the efficiency of the device, as mentioned previously.

Figure 6:
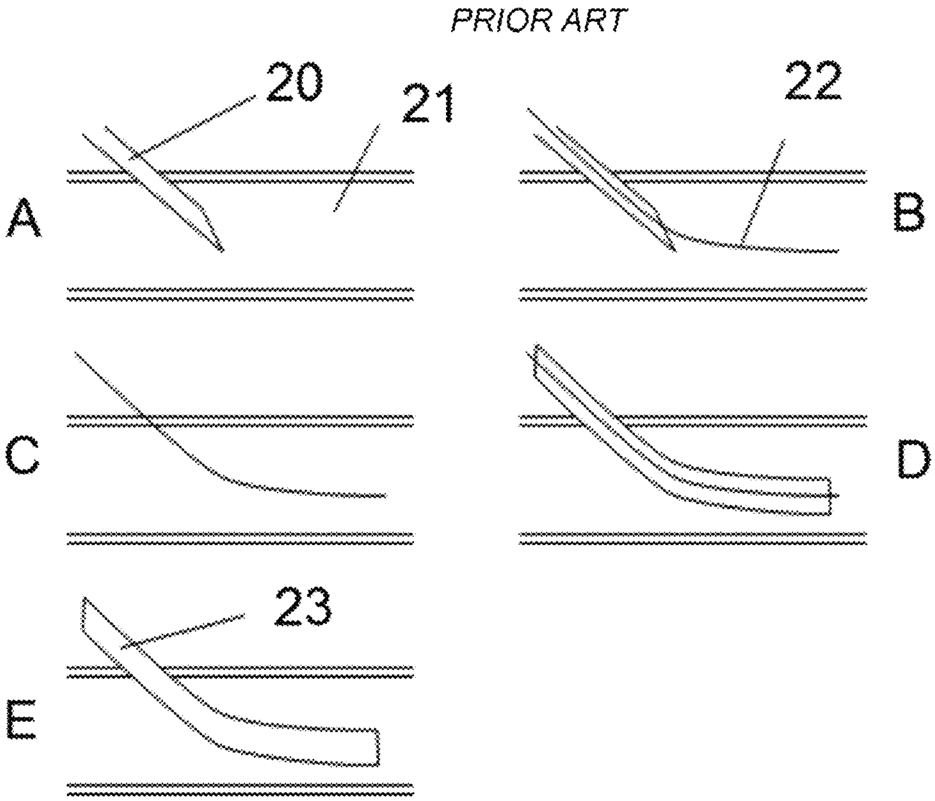
FIG. 6 illustrates the steps of the Seldinger method.

FIG. 6 illustrates the Seldinger technique for accessing an organ or a vein. Alternative techniques are known and the Seldinger technique is illustrated merely as an example of a way in which a medical professional may obtain access to an organ, such as a vein. A medical professional performs a puncture with a needle 20 (step A) in order to gain access to e.g. a vein 21 (or other hollow organ) and a guidewire 22 passes through the hollow needle and the puncture in the skin (step B). Then, the needle is withdrawn while the guidewire 22 remains inside of the vein or the hollow organ (step C). A surgical blade may be used to increase the incision in the skin to allow a catheter to reach the vein as well (step D). The use of introductory catheters, and dilators is known. The guidewire may be steered through the vasculature of a patient to reach a treatment site. A catheter (balloon catheter, stent, treatment catheter, or other) can be delivered to the treatment site by passing over the guidewire so as to allow investigation or treatment at a selected site. The guidewire might then be retracted (step E). In other interventions, the guidewire may stay in place. Depending on the intervention, multiple catheters may be used which may be retracted and a subsequent catheter might then be introduced and may be guided again by the guidewire.

For different interventions, it may be important to maintain the position of the guidewire(s) and various catheters in place as has already been discussed.

Figure 7:
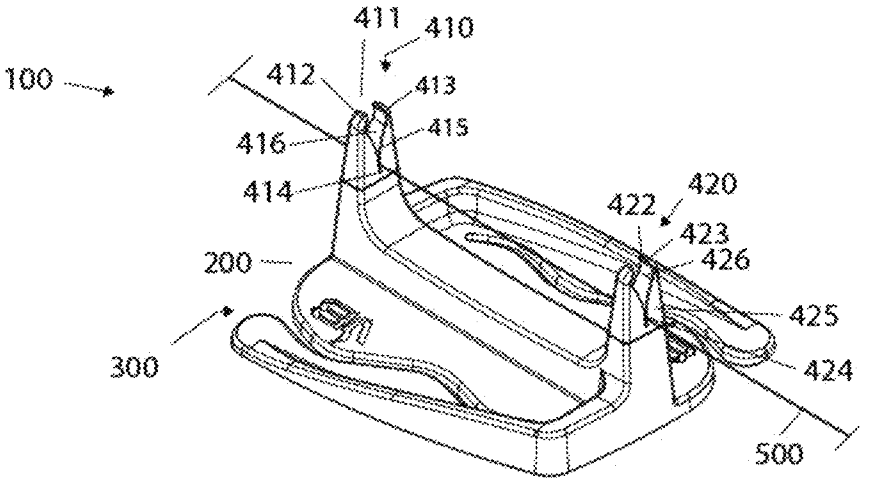
FIG. 7 illustrates an example of a support device supporting a guidewire.
Figure 8:
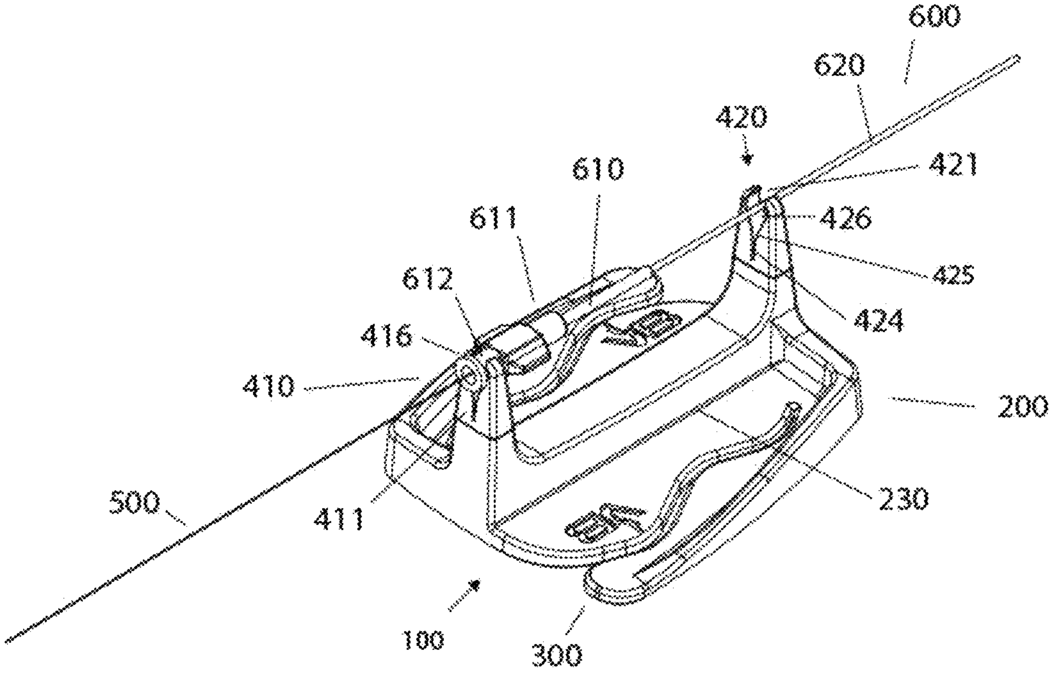
FIG. 8 illustrates an example of a support device supporting a catheter.
Figure 9A:
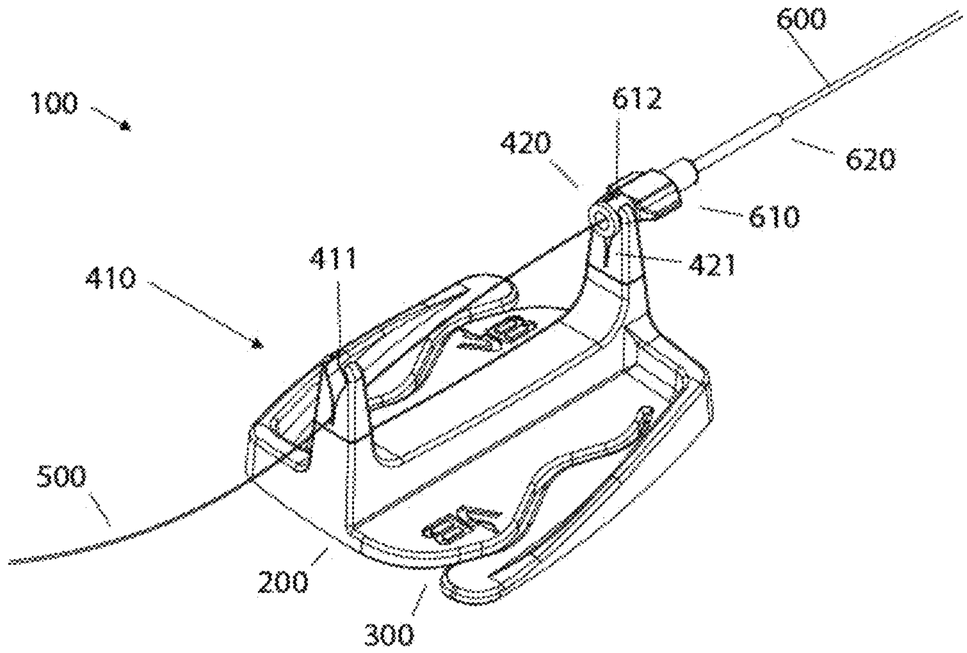
FIGS. 9A-9C illustrate an example of a use of a support device for supporting an elongated medical instrument.
Figure 9B:
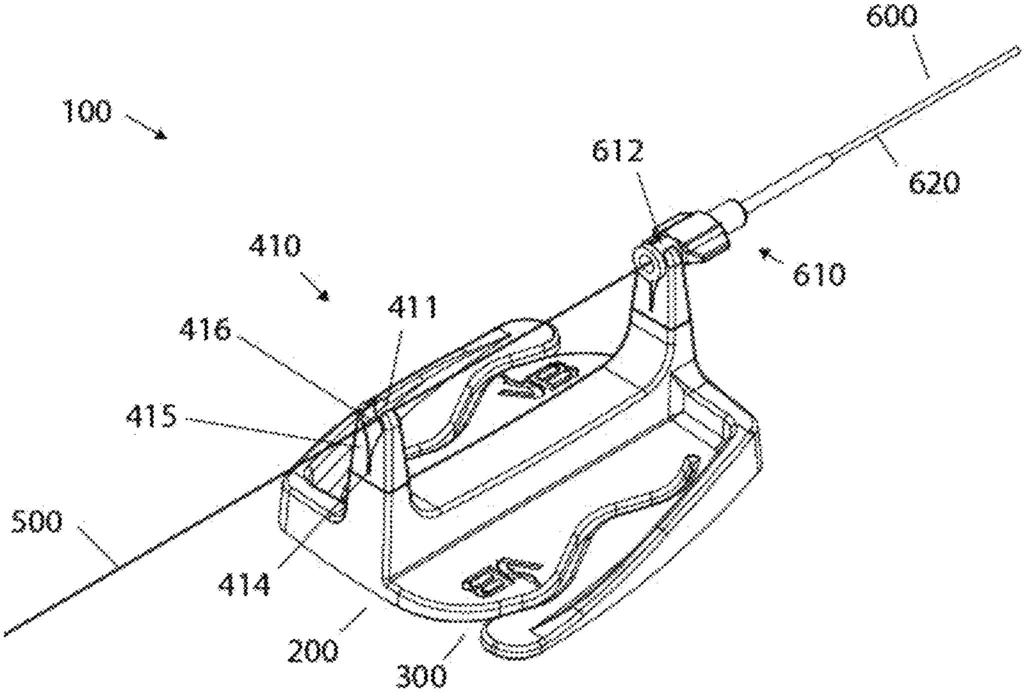

FIGS. 7-9 illustrate different implementations of device 100 for retaining at least an elongated medical instrument, e.g. a catheter 600 and/or a guidewire 500, when during an intervention different elongated medical instruments may be used. Although only a number of implementations will be described, other implementations are possible. Device 100 comprises a base 200, a gripping system 300 for securing the device to a fabric, e.g. surgical towel, and at least two retaining members 410, 420 disposed on the base 200 and extending upwardly from the base. In FIG. 7, a guidewire is retained in the two retaining members which are arranged one behind the other.

As illustrated in FIG. 8, in another intervention or at a different moment of the same intervention, the catheter 600 arranged around guidewire 500 may be supported by the device 100. Catheter 600 comprises a proximal body 610 and an insertion tube 620, configured to be inserted into the body of the patient and reach the site that is needed to be treated. Catheter's body 610 comprises a hub 611, wherein the hub 611 further comprises a neck 612, wherein said neck 612 has a standardized diameter. The catheters used on a day-to-day practice for interventional operations have necks 612 with the same diameter. Thus, a device 100 with retaining members 410, 420 may be suitable for retaining such catheters. In this example, retaining members 410, 420 with slits 411, 421 that comprise at least a third, substantially round or substantially O-shaped, segment 416, 426 (as, for example, illustrated in FIG. 3B), are implemented in order to retain the neck 612 of catheter 600 to the device 100. In this example, catheter 600 is grabbed in two points along its length such that the neck 612 of the catheter is fixed in the slit 411 of the retaining member 410 and a point of the insertion tube 620 is fixed in the slit 421 the retaining member 420.

The catheters used in most interventions have insertion tubes that their diameters ranging from e.g. 3 to 34 French gauge depending on the intended use.

A support device 100 may also be used to retain a guidewire 500 and a catheter 600, as illustrated in FIG. 9A. In this example, a guidewire 500 and a catheter 600 are retained on device 100, by fixing the guidewire 500 on the slit 411 of the retaining member 410 and by fixing the catheter 600 on the slit 421 of the retaining member 420. The catheter is fixed in slit 421 by fixing the neck 612 of catheter 600 as described in FIG. 8 and the guidewire is fixed into the slit 411 of the retaining member 410 of the device 100 as described in FIG. 7. The operator may place the guidewire 500 and the catheter 600 to the slits and then he may press down such instruments into the slits in order to secure them. This implementation 100 provides an efficient manner to retain a pair of elongated medical instruments, wherein one instrument is threaded into the other, thus, resulting in an important contribution of such device to the entire process of intervention by facilitating an operator to perform other aspects of an intervention rather than holding the medical instruments in place.

Figure 9C:
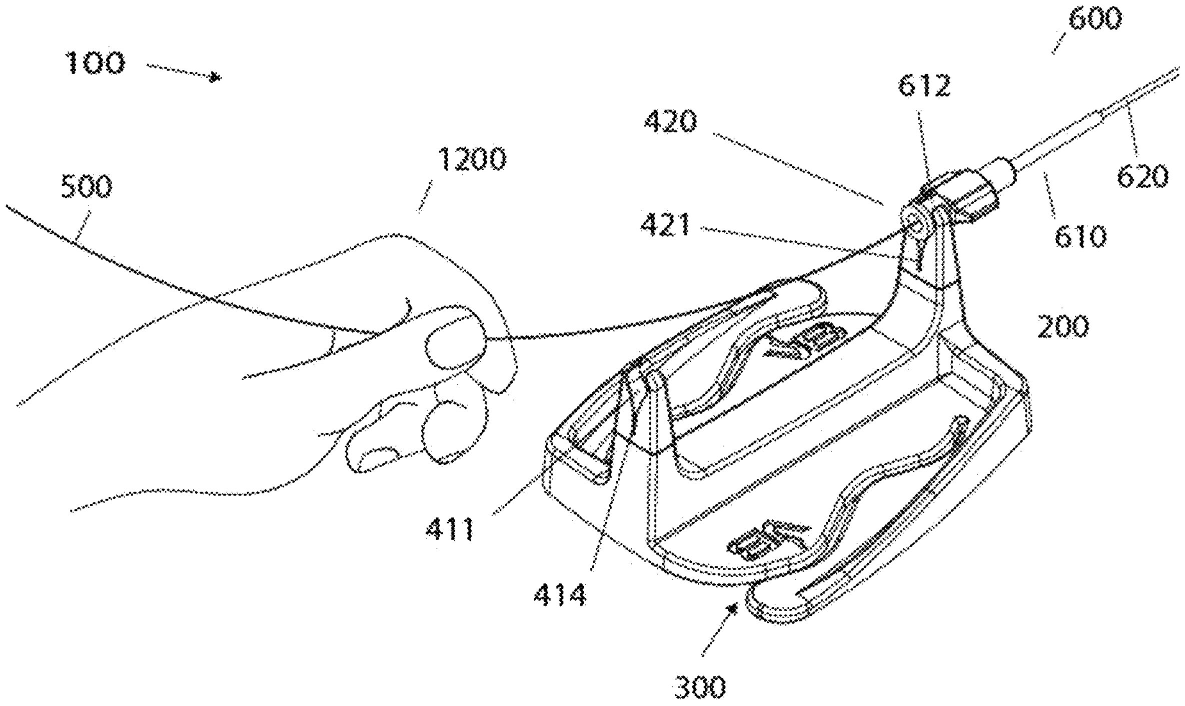

In an alternative way, the guidewire 500 and the catheter 600 are retained on device 100, by placing the guidewire 500 in the slit 411 and by fixing the catheter 600 on the slit 421 of the retaining member 420. The catheter is fixed in the slit 421 by fixing the neck 612 of catheter 600 as described in FIG. 8. However, in this example, the guidewire 500 is not secured in the first segment 414 of the of slit 411, but it passes through the third, O-shaped, segment 416 of slit 411 without being fastened strongly. Such an assembly facilitates exchanging guidewires from catheter 600, depending on the procedure of the intervention, while the catheter is secured on slit 421 (FIG. 9C). Upon completion of such exchanging of guidewires, the operator 1200 may secure the guidewire once again in the slit 411, and in particular in segment 414 of the slit, as illustrated in FIG. 9*a*.

Figure 10A:
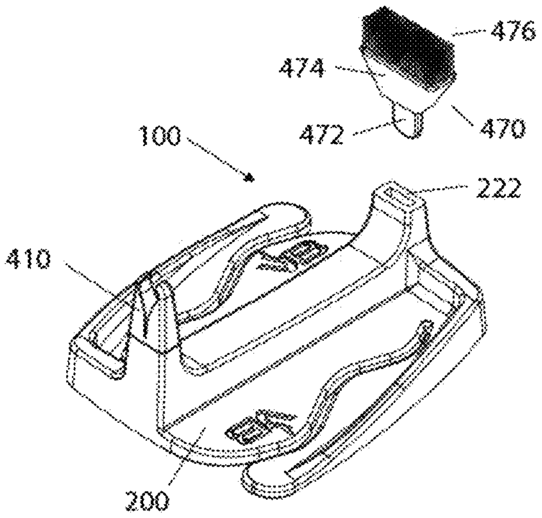
FIGS. 10A and 10B illustrate a further example of a support device.
Figure 10B:
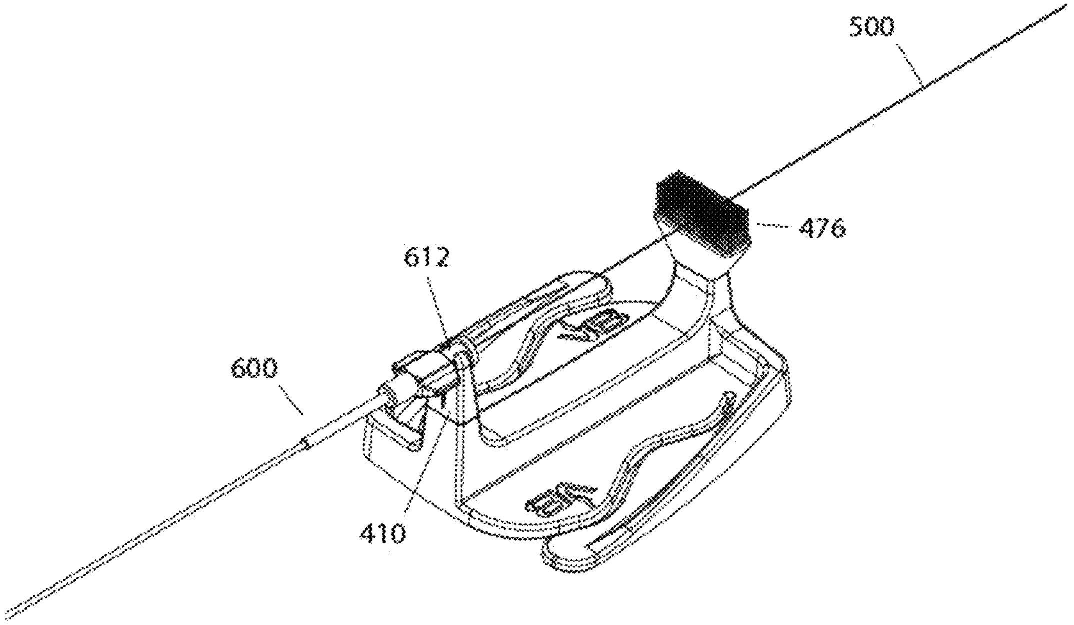

FIGS. 10A and 10B illustrate a further example of a support device 100. In this example, one of the retaining members is different from the retaining members previously illustrated for other support devices 100. The retaining members in this example may be detachably fixed to the base 200. The detachable retaining member 470 may be placed in coupling 222 by a user, wherein said couplings may be part of an elevated portion 220 of the base 200. The retaining member 470 comprises a corresponding connector 472 that mates with coupling 222. In this particular example, the attachment between retaining members 470 and the couplings 222 is a male-female coupling. In any of the illustrated examples, the retaining members 470 may be snap fit in coupling 220.

Retaining member 470 further has a base on which a plurality of pins 476 is provided. A thin elongated medical device may be retained in between pins 476. One or more rows of pins 476 may be provided to create a plurality of retaining members next to each other. In this particular example, the retaining member has a brush-like or comb-like appearance with a plurality of rows of pins behind each other.

FIG. 10B schematically illustrates how a guidewire 500 may be retained in between pins 476. The guidewire 500 may be used in an intervention to guide catheter 600. At the other retention member 410, a neck 612 at a proximal end of catheter 600 is being retained in the situation of FIG. 10*b*.

Figure 11A:
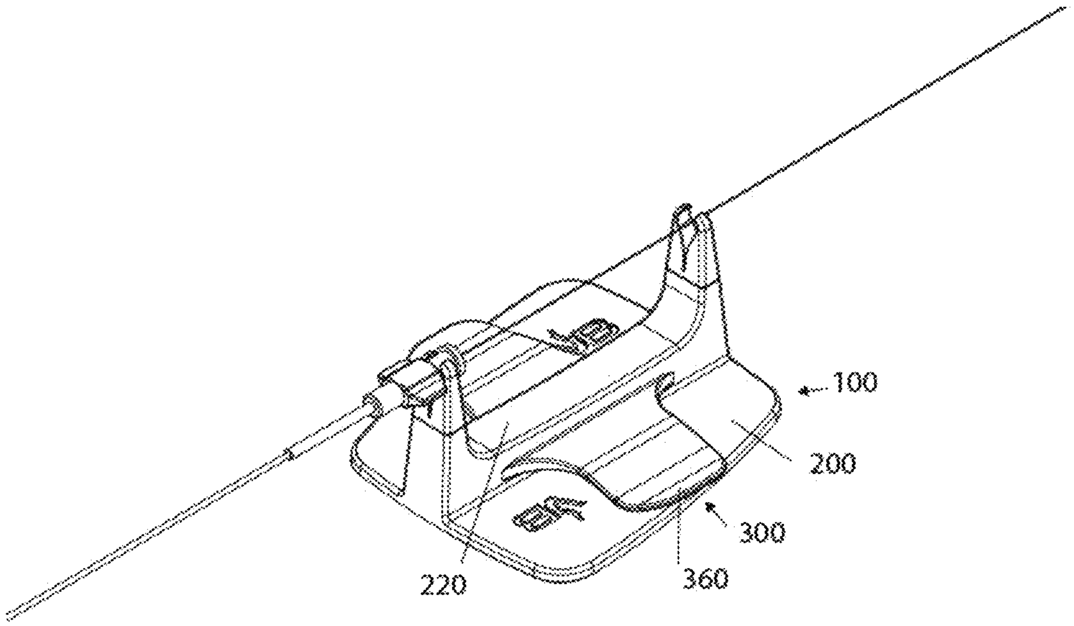
FIGS. 11A and 11B illustrate yet a further example of a support device.
Figure 11B:
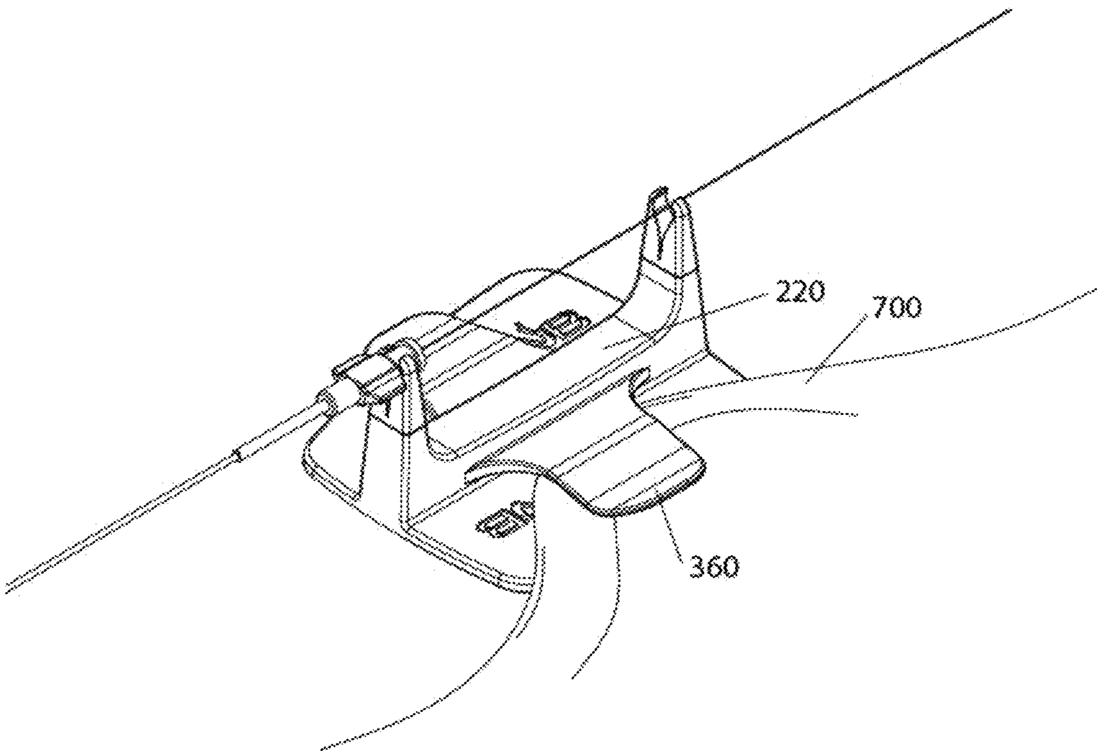

FIGS. 11A and 11B illustrate yet a further example of a support device 100 with an alternative gripping system 300. In the illustrated example, surgical towel 700 may be gripped and secured between a wing 360 and base 200. The wing 360 may pivot with respect to base 200, and specifically with respect to a centric portion. The wing may have resiliency and/or may be spring loaded. In the illustrated example, two wings 360 are provided on a single support device 100. In a default position, the wing(s) may bear down on the base 200, but a user may open the wing to clamp the surgical towel in between base 200 and wing 360. In the illustrated example, the device includes one wing on each side of the retaining members. In alternative examples, a single wing 360 may be used, or multiple smaller wings may be used on one or both sides of the retaining members.

Figure 2A:
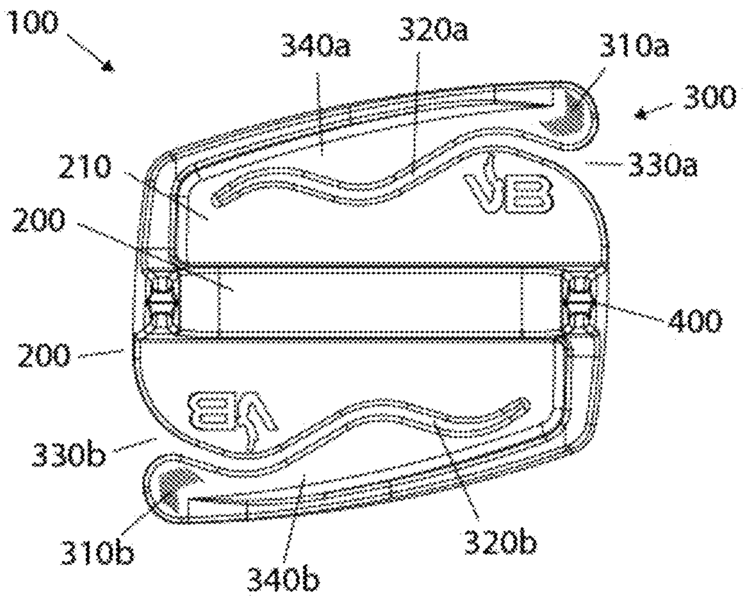
FIG. 2A illustrates a top view of the support device of FIG. 1B having a gripping system to secure the device in place to support an elongated medical instrument.
Figure 2B:
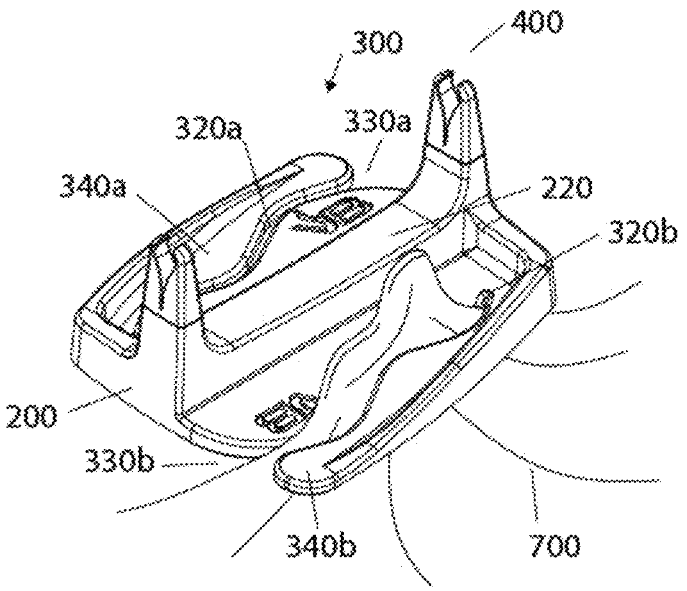
FIG. 2B illustrates an isometric view of the support device of FIG. 2A with the support device gripped on a surgical towel.

In yet a further non-illustrated example, a gripping may system may be provided in which fingers 340 (as in e.g. FIG. 2) may have a flat inner side that can rest against a side of base 200. Such a finger may have some flexibility or include a spring to force the finger in contact with the base. A user may open the finger and introduce a portion of surgical towel in between the finger and the base. The finger can then clamp the surgical towel.

In any of the examples disclosed herein, the base of the support devices may be substantially rectangular. The length of the support devices in the examples may be between 5 and 20 cm. Specifically, the support device may have a length between 7 and 15 cm. More specifically, the support device may have a length between 8 and 12 cm. The width of the support devices in the examples may be between 5 and 15 cm. Specifically, the support device may have a width between 7 and 12 cm. More specifically, the support device may have a width between 6 and 9 cm. The height of the support devices may be between 1 and 10 cm. Specifically, the height of the support device may be between 3 and 7 cm. In one specific example, the support device has a length between 8 and 12 cm, a width between 6 and 9 cm and a heath between 3 and 7 cm.

FIGS. 12A-12D schematically illustrate yet a further example of a support device. The support device 1000 illustrated in FIG. 12 comprises a plurality of sets 400A, 400B, 400C, 400D of retaining members. Each set of retaining members 400A-400D in this example comprises a first retaining member disposed behind a second retaining member substantially along the first direction. In this particular examples, the support device 1000 comprises four sets of retaining members.

Within the endovascular procedures that are performed using guides and catheters, increasingly complex procedures have been developed that use more than one guide simultaneously through a vascular access. A vascular access is the entry point of certain medical devices in the form of guides, catheters or others that are introduced into the body through a system named introducer or sheath, which allows to keep these devices in a stable way inside the vessels (arteries or veins).

There are procedures for the implantation of fenestrated endoprostheses that require the catheterization of a plurality of vessels, e.g. at least three to four vessels in sequence for their implantation but that require stabilization for a period of time, e.g. 30 minutes or more. The actual time will depend on the speed of catheterization and the implantation of the branches.

Specifically, endoprosthesis systems may treat and/or access the aorta, the superior mesenteric artery, the two renal arteries (right and left) and the celiac trunk. These guides are usually introduced from the same port or access or introducer (at the femoral or axillary level) for which the manipulation must be very precise and great caution must be maintained to avoid sudden movements that cause loss of location.

To ensure that once they have been catheterized, the correct position of the guides is not lost, it is important that each of the guides and/or catheters can be stabilized and maintained in their position. With the support device 1000, one can ensure the correct fixation of 4 guides or guide/catheter combinations simultaneously. In the illustrated example, the base 200 includes identifying marks or letters of each of the guides to facilitate control over the exact position of each guide.

In this examples CT indicates celiac trunk, SM indicates superior mesenteric, RR indicates right renal and LR indicates left renal. It will be clear that these letters and indications may be varied for different applications. In alternative examples, e.g. two or three guides or guide/catheter combinations may be used, and the support device 1000 may be adapted for a specific need or intervention.

Figure 12A:
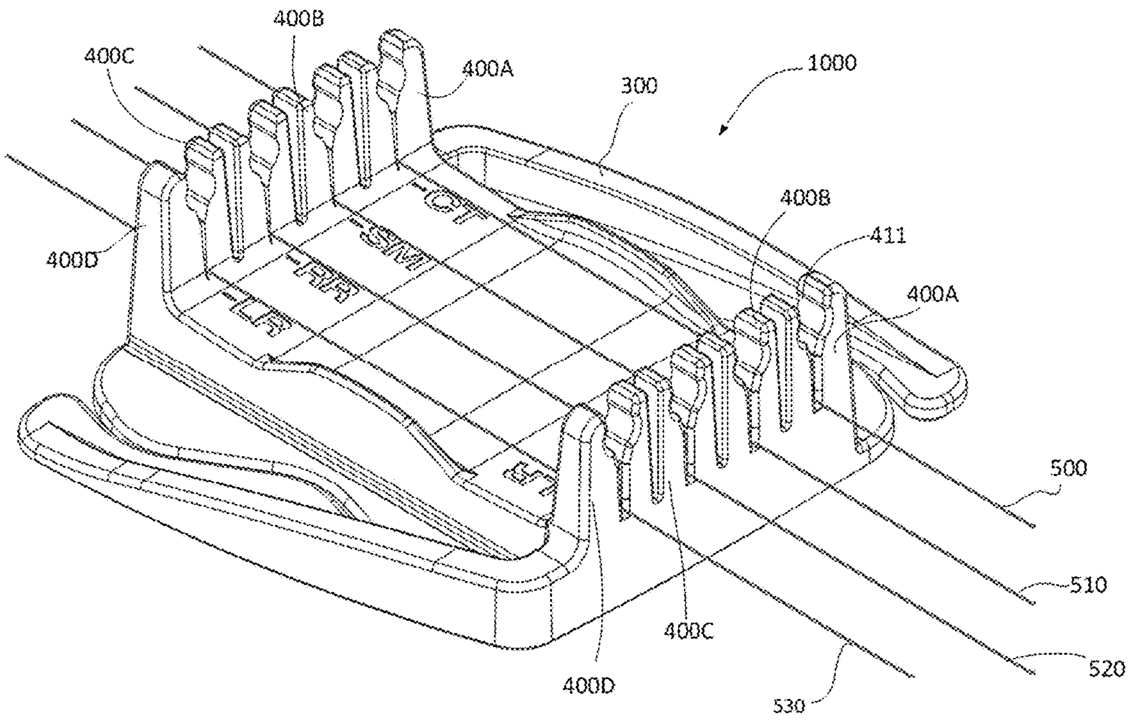
FIGS. 12A-12D schematically illustrate yet a further example of a support device.

With reference to FIG. 12A, the support device 1000 comprises four sets of retaining members. Each of the sets 400A-400D comprises a first and a second retaining member arranged one behind the other, such that an elongated medical device can be clamped or otherwise fixed in position along two different portions of the same medical device.

Set 400A in this example is intended to fix in place an elongated medical device that accesses the celiac trunk. Guidewire 500 is fixed in both retaining members arranged one behind the other. Guidewire 510 is fixed at two different portions of the guidewire by the set 400B of retaining members. Guidewire 510 in this example may be used to access and/or treat the superior mesenteric artery. Similarly guidewires 520 and 530 used for treating and/or accessing the right renal and left renal artery respectively are fixed in position by sets 400C and 400D of retaining members.

Similarly as in hereinbefore described examples, the support device 100 may include a gripping system 300 for securing the base 200 to a surgical towel.

Figure 12B:
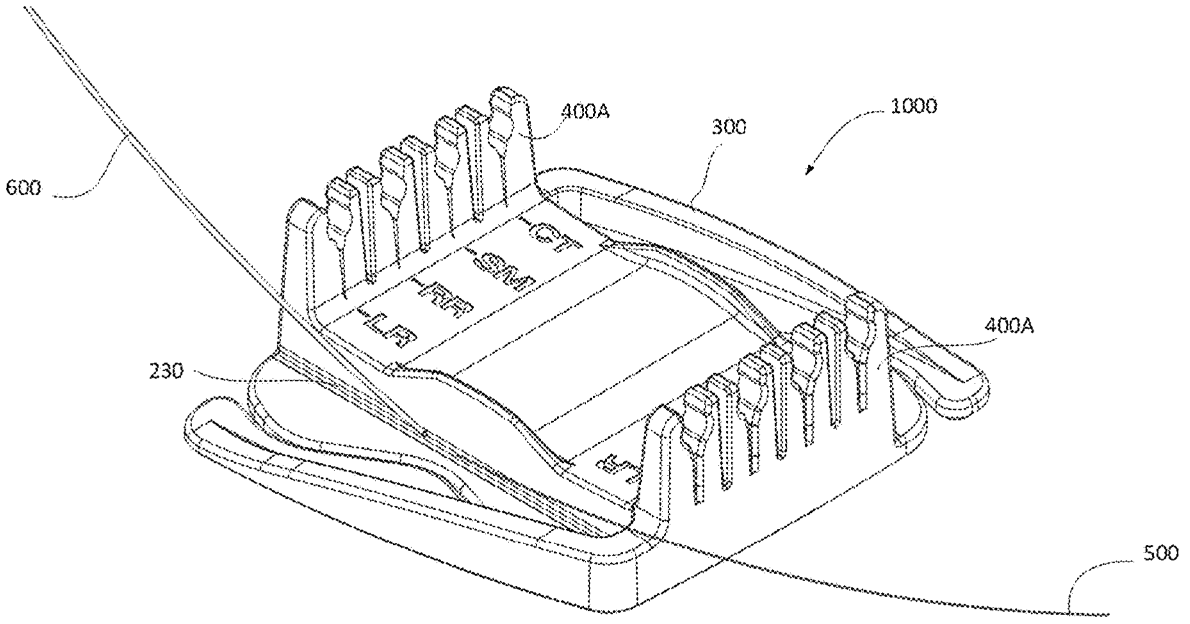

As shown in FIG. 12B, support device 1000 may include one or more grooves 230 configured for guidewire threading. A tube of catheter 600 may be positioned in groove 230, and guidewire 500 may be positioned in groove 230 as well. Using the groove 230, the guidewire 500 can be pushed towards catheter 600 and introduced into it. Only one groove 230 for guidewire threading is shown at a side of the support device 100 between retaining members 400D and gripping system 300. A similar groove may be incorporated at the opposite side of the support device 100 i.e. between retaining members 400A and gripping system 300.

Figure 12C:
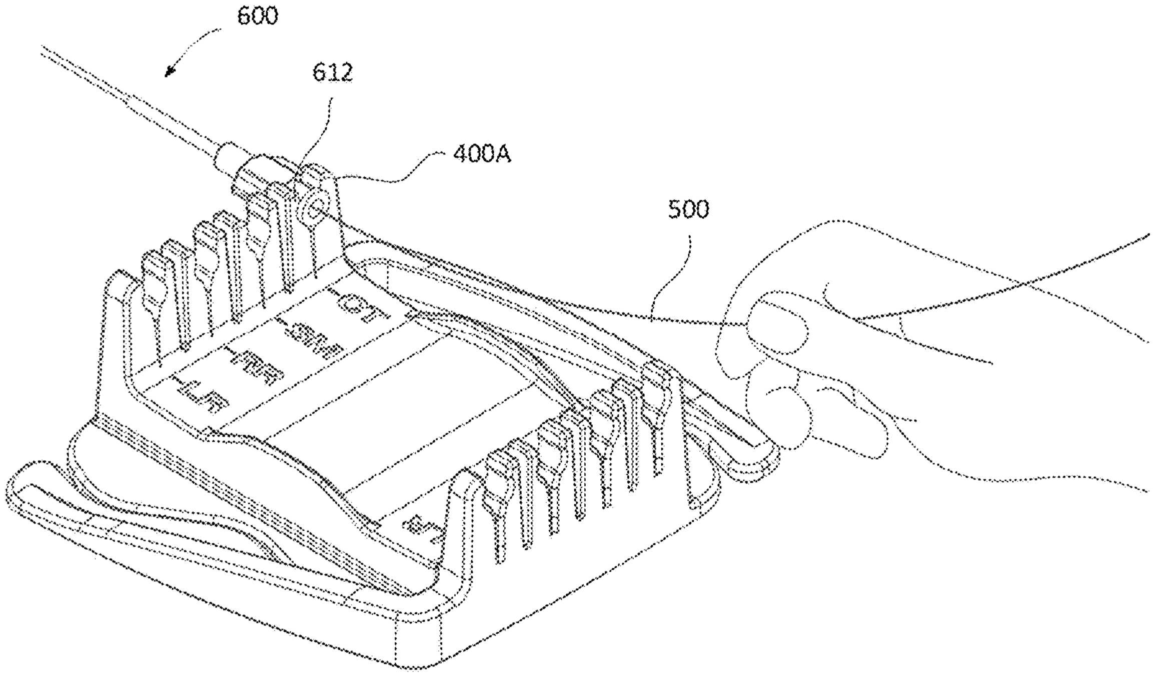
Figure 12D:
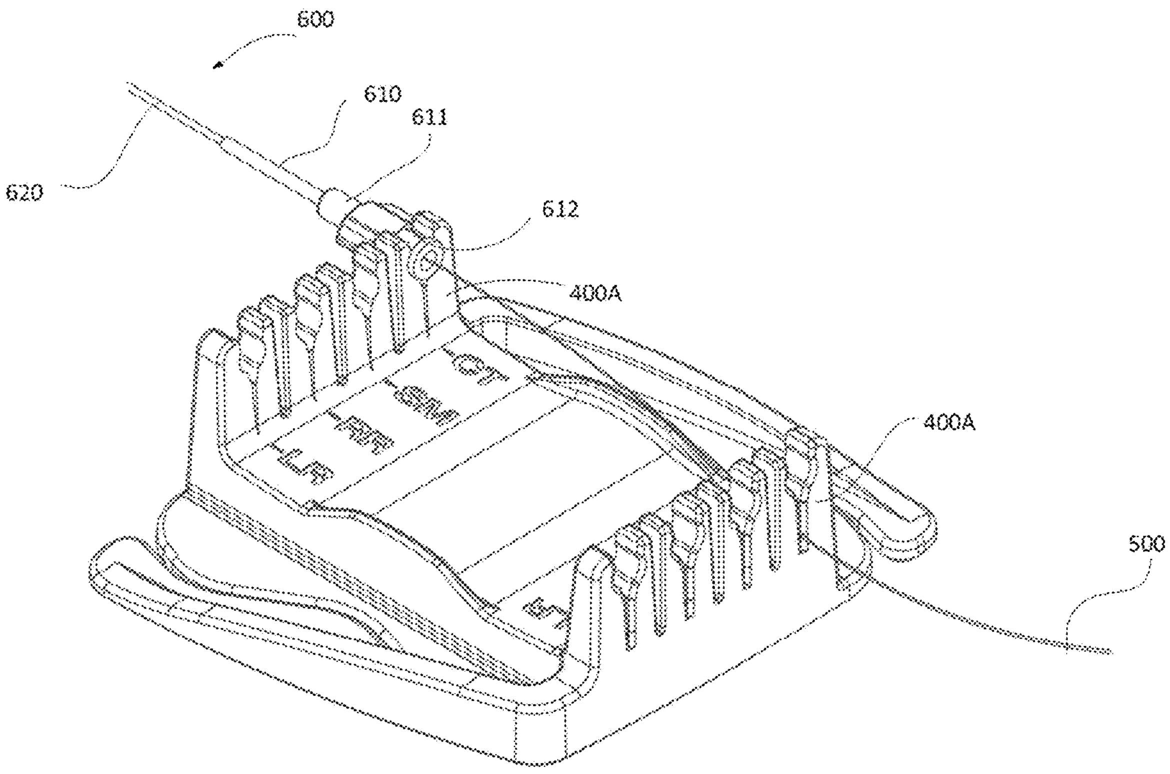

FIGS. 12C and 12D schematically illustrates how a catheter may be fixed in a first of the set of retaining member 400A, and a guidewire 500 may be fixed in a second of the same set of retaining members 400A. Catheter 600 comprises a proximal body 610 and an insertion tube 620, configured to be inserted into the body of the patient and reach the site that needs to be treated. Catheter's body 610 comprises a hub 611, wherein the hub 611 further comprises a neck 612, wherein said neck 612 has a standardized diameter. Neck 612 may be fixed in retaining member 400A.

As illustrated in FIG. 12C, during an intervention, the catheter may remain fixed in position by the clamping force of the first of the retaining members 400A. At the same time, the guidewire may be repositioned and moved with respect to the catheter. A medical professional may remove the guidewire from the support device, reposition and fix (like in FIG. 12*d*) the guidewire 500 in the second of the set of retaining members 400A.

For reasons of completeness, several aspects of the present disclosure are set out in the following numbered clauses:

Clause 1. A support device for supporting an elongated medical instrument comprising:

- a base;
- a gripping system for securing the base to a surgical towel; and
- at least two retaining members disposed on the base and extending upwardly from the base, the retaining members having a slit configured to support the elongated medical instrument, such that the elongated medical instrument extends through the slit of the retaining members substantially along a first direction, and wherein
- a first of the at least two retaining members is disposed behind a second of the retaining members substantially along the first direction.

Clause 2. The support device of clause 1, wherein the retaining members are formed integrally with the base.

Clause 3. The support device of clause 1, wherein the retaining members or part of the retaining members are detachably fixed to the base.

Clause 4. The support device of clause 3, wherein the retaining members are configured for a single use.

Clause 5. The support device of clause 3 or 4, wherein the retaining members are made from a first material, and the base is made from a second material, the first material being different from the second.

Clause 6. The support device of any of clauses 1-5, comprising two or more sets of retaining members, each set of retaining members comprising a first retaining member disposed behind a second retaining member substantially along the first direction.

Clause 7. The support device of clause 6, comprising four sets of retaining members.

Clause 8. The support device of clause 6 or 7, wherein the base comprises one or more identification marks for indicating an elongated medical instrument to be position in one or more set of retaining members.

Clause 9. The support device of any of clauses 1-8, wherein the slits of one or more of the retaining members comprise a first segment, and a second segment, wherein the first segment is located below the second segment, and wherein the first segment is narrower than the second segment.

Clause 10. The support device of clause 9, wherein the first segment has a substantially constant width.

Clause 10. The support device of clause 9, wherein the second segment has a substantially V-shaped cross-section.

Clause 11. The support device of clause 10, wherein an angle between a first surface and a second surface forming the second segment is between 2° and 20°.

Clause 12. The support device of any of clauses 8-10, wherein the slit comprises a third segment and wherein the second segment is located below the third segment.

Clause 13. The support device of clause 11, wherein the third segment has a rounded or substantially ovaloid cross section.

Clause 14. The support device of clause 9, wherein the second segment has a rounded or substantially ovaloid cross-section.

Clause 15. The support device of any of clauses 1-14, wherein the first retaining member has a different shape and/or different dimensions than the second retaining member.

Clause 16. The support device of any of clauses 1-15, wherein the gripping system is formed by a first opening in the base extending substantially along the first direction from a first edge of the base.

Clause 17. The support device of clause 16, wherein the opening is substantially sinusoidal.

Clause 18. The support device of clause 16 or 17, further comprising a second opening extending from a second edge of the base, opposite to the first edge and extending along the first direction.

Clause 19. The support device of any of clauses 1-18, wherein the base has a portion with increased roughness for gripping, and optionally wherein the portion with increased roughness.

Clause 20. The support device of any of clauses 1-19, wherein the base comprises one or more grooves configured for guidewire threading.

Clause 21. The support device of clause 20, wherein the one or more grooves for guidewire threading are formed between the gripping system and the retaining members and extend substantially along the first direction.

Clause 22. The support device of any of clauses 1-21, wherein the elongated medical instruments are guidewires and/or catheters.

Clause 23. The support device of any of clauses 1-22, wherein the support device is configured to be used and sterilized more than once.

Clause 24. The support device of clause 23, wherein the support device is made of stainless steel.

Clause 25. The support device of any of clauses 1-24, wherein the device is configured for a single-use.

Clause 26. The support device of clause 25, wherein the device is made of a polymer.

Clause 27. The device of any of clauses 1-26, wherein the retaining members are configured to receive the elongated medical instruments with a diameter ranging from 0,254 mm to 11.3 mm.

Although only a number of examples have been disclosed herein, other alternatives, modifications, uses and/or equivalents thereof are possible. Thus, the scope of the present disclosure should not be limited by particular examples, but should be determined only by a fair reading of the claims that follow.

What is claimed is:

1. A support device for supporting an elongated medical instrument comprising:

- a base;
- a gripping system for securing the base to a surgical towel; and
- first and second retaining members disposed spaced-apart from one another on the base and extending upwardly from the base,
- the first retaining member having a first slit configured to receive a first part of the elongated medical instrument so that the first part is supported by the first retaining member, the second retaining member having a second slit configured to receive a second part of the elongated medical instrument so that the second part is supported by the second retaining member, the first and second slits being aligned with one another along a first direction such that when the elongated medical instrument extends through the first and second slits, a portion of the elongated medical instrument located between the first and second slits extends along the first direction, the first direction pointing from a front edge of the base to a rear edge of the base, each of the first and second slits including a first segment having a constant width in a transverse direction and a second segment entirely comprising a V-shaped cross-section in the transverse direction, the transverse direction being orthogonal to the first direction, the first segment being located directly below the second segment and the first segment being narrower than the second segment, the first segment being a lowest segment in each of the first and second slits;

each of the first and second slits comprises a third segment having a rounded or an ovaloid cross section in the transverse direction, the second segment being located directly below the third segment of the corresponding first and second slit, the first segment being configured to retain a first guidewire, the second segment being configured to retain a second guidewire, the third segment being configured to retain a catheter, wherein the gripping system is formed by a first opening in the base having a sinusoidal shape and extending from the front edge of the base towards the rear edge of the base, an amplitude of the sinusoidal shape being defined in the base in the transverse direction.

2. The support device of claim 1, wherein the first and second retaining members are formed integrally with the base.

3. The support device of claim 1, wherein the first and second retaining members or a part of each of the first and second retaining members are detachably fixed to the base.

4. The support device of claim 3, wherein each of the first and second retaining members is made from a first material, and the base is made from a second material, the first material being different from the second material.

5. The support device of claim 1, wherein the first retaining member has a different shape and/or different dimensions than the second retaining member.

6. The support device of claim 1, wherein the gripping system further comprises a second opening extending from the rear edge of the base.

7. The support device of claim 1, further comprising third and fourth retaining members that are disposed spaced-apart from one another on the base and extend upwardly from the base, the third and fourth retaining members disposed aligned with one another along the first direction.

8. A support device for supporting an elongated medical instrument comprising:

a base;

a gripping system for securing the base to a surgical towel; and first and second retaining members disposed spaced-apart from one another on the base and extending upwardly from the base, the first retaining member having a first slit configured to receive a first part of the elongated medical instrument so that the first part is supported by the first retaining member, the first retaining member being arranged at a front edge of the base, the second retaining member having a second slit configured to receive a second part of the elongated medical instrument so that the second part is supported by the second retaining member, the second retaining member being arranged at a rear edge of the base, the first and second slits being aligned with one another along a first direction such that when the elongated medical instrument extends through the first and second slits a portion of the elongated medical instrument located between the first and second slits extends along the first direction, the first retaining member being disposed behind the second retaining member along the first direction, and one or both of the first and second slits including a first segment, a second segment and a third segment, the first segment being located directly below the second segment, and the second segment being located directly below the third segment, the first segment having a constant width in a transverse direction, the second segment entirely comprising a V-shaped cross-section in the transverse direction, and the third segment having a rounded or ovaloid cross-section in the transverse direction, the transverse direction being orthogonal to the first direction, and wherein the gripping system is formed by a first opening in the base having a sinusoidal shape and extending from the front edge of the base towards the rear edge of the base, an amplitude of the sinusoidal shape being defined in the base in the transverse direction.

9. The support device of claim 8, wherein an angle between a first surface and a second surface forming the second segment is between 2° and 20°.

10. A support device for supporting a guidewire and a catheter comprising:

a base having a front edge and a rear edge;

a gripping system for securing the base to a surgical towel; and first and second retaining members disposed spaced-apart on the base and extending upwardly from the base, the first retaining member being closer to the front edge of the base than to the rear edge of the base, the second retaining member being closer to the rear edge of the base than to the front edge of the base, the gripping system is formed by a first opening in the base having a sinusoidal shape and extending from the front edge of the base towards the rear edge of the base an amplitude of the sinusoidal shape being defined in the base in a transverse direction, the first retaining member having a first slit configured to receive a part of the guidewire so that the part of the guidewire is supported by the first retaining member, the second retaining member having a second slit configured to receive a part of the catheter so that the part of the catheter is supported by the second retaining member, the first and second slits being aligned with one another along a first direction such that when the guidewire or catheter extends through the first and second slits a portion of the guidewire or catheter located between the first and second slits extends along the first direction, the first direction being orthogonal to the transverse direction, the second slit including a first segment, a second segment, and a third segment, the first segment being located directly below the second segment, and the second segment being located directly below the third segment, the first segment being narrower in the transverse direction than the second segment, and the third segment having a rounded or ovaloid cross section in the transverse direction configured to retain a neck of a hub of the catheter.

11. The support device of claim 10, wherein the first segment and/or the second segment is configured to retain the guidewire.

12. The support device of claim 1, wherein the first segment and the second segment are vertically aligned.

* * * * *